US007880878B2

(12) United States Patent
McCawley et al.

(10) Patent No.: US 7,880,878 B2
(45) Date of Patent: Feb. 1, 2011

(54) PARTICLE COUNTING AND DNA UPTAKE SYSTEM AND METHOD FOR DETECTION, ASSESSMENT AND FURTHER ANALYSIS OF THREATS DUE TO NEBULIZED BIOLOGICAL AGENTS

(75) Inventors: Michael McCawley, Morgantown, WV (US); Simon Goetze, Alexandria, VA (US); Phillip Green, II, Clarksburg, WV (US); Jeannette Hoy, Fairmont, WV (US); Bernard McGee, Wheeling, WV (US)

(73) Assignee: Respiratory Management Technology, Morgantown, WV (US)

( * ) Notice: Subject to any disclaimer, the term of this patent is extended or adjusted under 35 U.S.C. 154(b) by 0 days.

(21) Appl. No.: 12/814,883

(22) Filed: Jun. 14, 2010

(65) Prior Publication Data

US 2010/0253944 A1    Oct. 7, 2010

Related U.S. Application Data

(62) Division of application No. 11/490,525, filed on Jul. 21, 2006, now Pat. No. 7,738,100.

(60) Provisional application No. 60/701,035, filed on Jul. 21, 2005.

(51) Int. Cl.
   *G01N 15/02*  (2006.01)
(52) U.S. Cl. .................... 356/336; 356/51; 356/417; 356/317; 250/458.1
(58) Field of Classification Search ......... 356/335–343, 356/51, 300, 317, 417, 301; 250/459.1, 458.1
See application file for complete search history.

(56) References Cited

U.S. PATENT DOCUMENTS

| | | | |
|---|---|---|---|
| 2,732,753 A | | 1/1956 | O'Konski |
| 5,085,500 A | | 2/1992 | Blesener |
| 5,895,922 A | * | 4/1999 | Ho .......................... 250/492.1 |
| 6,787,302 B2 | | 9/2004 | Fleming et al. |
| 7,356,163 B2 | | 4/2008 | Beckert et al. |
| 2003/0144200 A1 | | 7/2003 | Baird et al. |
| 2005/0243307 A1 | | 11/2005 | Silcott et al. |
| 2006/0134397 A1 | * | 6/2006 | Smith ...................... 428/304.4 |
| 2007/0013910 A1 | | 1/2007 | Jiang et al. |
| 2009/0101843 A1 | * | 4/2009 | Henshaw et al. ......... 250/484.4 |
| 2009/0225322 A1 | * | 9/2009 | Henshaw et al. ............ 356/451 |
| 2010/0006760 A1 | * | 1/2010 | Lee et al. ................. 250/338.5 |
| 2010/0108910 A1 | * | 5/2010 | Morrell et al. ........... 250/459.1 |

* cited by examiner

*Primary Examiner*—Hoa Q Pham
(74) *Attorney, Agent, or Firm*—Connolly Bove Lodge & Hutz LLP

(57) ABSTRACT

The Nebulized Airborne Biohazard Stage Alert (NABSA) is a method utilizing an optical particle counter in conjunction with a fluorometer as triggers to detect and assess potential biohazard threats infused into surrounding air. In the first stage an optical particle counter is constantly passing sampled air in front of an energy source, in turn scattering light. This scattered light is evaluated to establish if the particles are above one micrometer in concentrations, and thus potentially an aerosolized threat. Such detection triggers the secondary stage in which the sample particles are tested for viability via processing through a dye with fluorescent properties affected when bonded with an entity universally found in all biological substances and a UV light source. The detection of concentrations of oversized, viable particles triggers the third stage to compare a sample of the particles to known biowarfare agents to delineate the specific agent species.

1 Claim, 2 Drawing Sheets

Functional Block Diagram of System

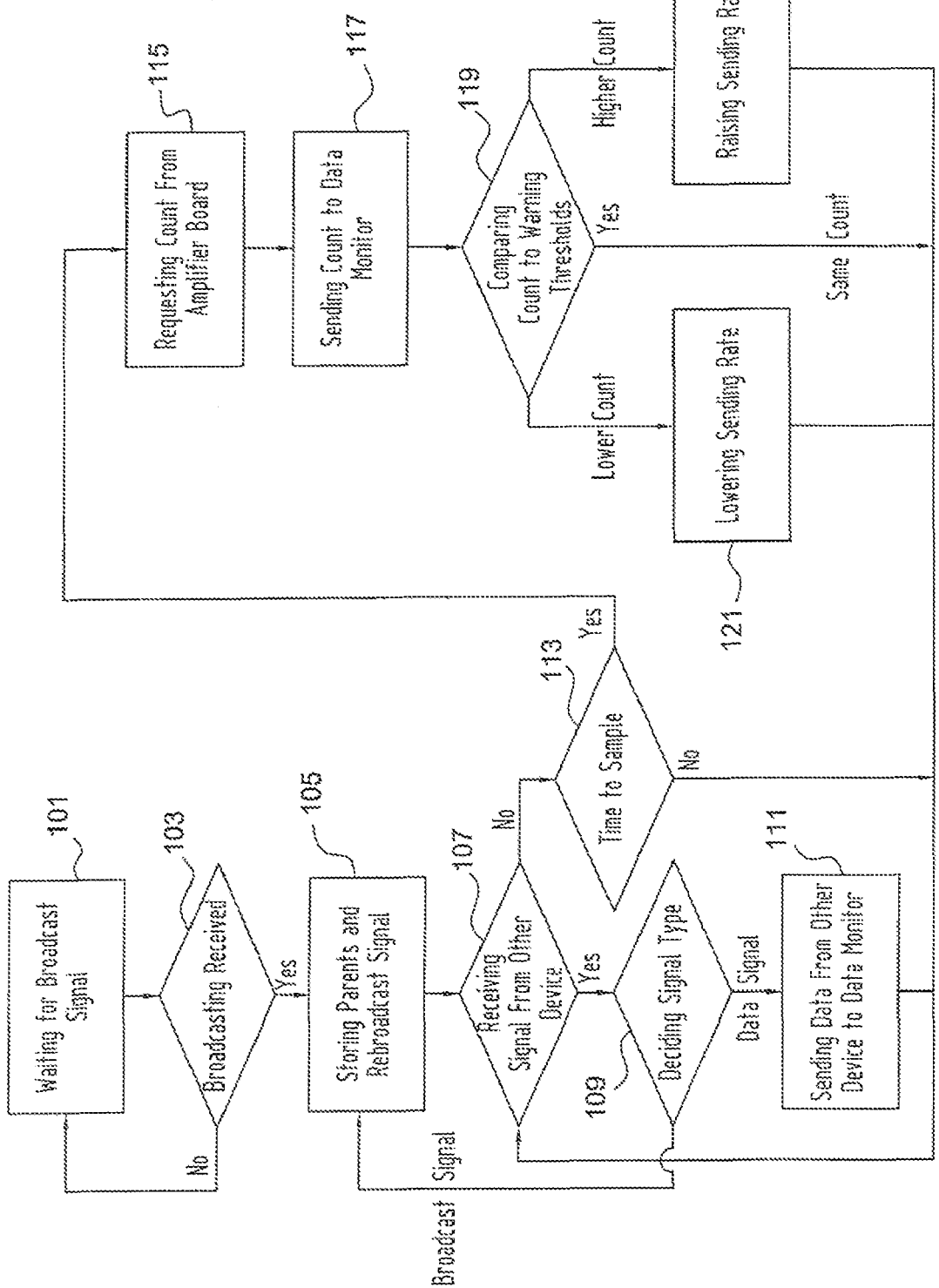
FIG. 2 Data Flow Diagram of Communications Subsystem

PARTICLE COUNTING AND DNA UPTAKE SYSTEM AND METHOD FOR DETECTION, ASSESSMENT AND FURTHER ANALYSIS OF THREATS DUE TO NEBULIZED BIOLOGICAL AGENTS

CROSS-REFERENCE TO RELATED APPLICATIONS

This application is a divisional of U.S. application Ser. No. 11/490,525, filed Jul. 21, 2006, allowed and assigned to U.S. Pat. No. 7,738,100, with an issue date of Jun. 15, 2010, which is a U.S. Non-Provisional Application of U.S. Provisional Application No. 60/701,035, filed Jul. 21, 2005, the entire contents of which are hereby incorporated herein by reference in their entireties.

FIELD OF THE INVENTION

The field of the invention is detecting and assessing threats due to nebulized biological agents. In particular, the present invention relates to detecting particles within a specific narrow size spectrum using an Optical Particle Counter (OPC).

BACKGROUND OF THE INVENTION

With the ever-growing threat of bioterrorist attacks, the development of technology to aid in the quick identification and possible counteraction of such attacks is merited. Bioterrorist attacks reach far beyond anthrax powder or food contamination. Aerosol technology aids in the infusion of biochemical threats into the air. In the past, it was more feasible to rely on laboratory settings for the examination of potential biowarfare agents, but at present people are confronted with more widespread threats and potential hoaxes making on-site testing essential. This is the type of threat technology to which an Optical Particle Counter (OPC) may be applied.

An OPC acts as an on-site, inexpensive, and widely disseminating detector for the carriers of these biochemical threat agents, as opposed to trying to detect the actual threat agents, which is a slower and more costly process. The OPC is an instrument based on the principle of light scattering from particles typically used to measure particles above 0.05 micrometers in diameter. Such instruments have been used by environmental engineers to measure size distribution of particulate pollutants in the ambient atmosphere, in exhausts of industrial devices such as smelters, coal combustors, and automobiles; also for measuring efficiencies of particle control equipment and also to calibrate other instruments. OPCs are also used by industrial hygienists to sample particles in occupational environments. Pharmacists use them to size and classify their powdered drugs.

Analysis of the size spectrum thereby reveals the presence of different sources of aerosol and alerts one to the introduction and presence of foreign, extraneous, sources to the average background. Flowing particles can be analyzed using light scattering techniques, in real time, in order to measure each particle's size. This aerosol spectrometry gives data on both the number and size of particles suspended in an air stream. Research has shown that the mean particle size based on the number distribution is substantially less than one micrometer. Thus, generation of particles larger than one micrometer, which is common for most biological aerosol generation systems, is easily detected against very low background number concentrations in any one micrometer-wide size range (at concentrations above 0.1 particles per cubic meter).

Examples of background art in this technical area include U.S. Pat. No. 2,732,753 to O'Konski, which determines the viability of particles using a dye with detectable fluorescent properties; and U.S. Pat. No. 6,787,302 to Fleming, which detects and quantifies viable cell samples using fluorescent dyes.

Yet another example of a background art method for particulate counting and a biomass indicator is the AMEBA Biosensor, which monitors physiological response data from microorganisms exposed to aerosolized samples. In addition, a Digital Smell/Electric Nose comprising: an array of gas sensors with different selectivity patterns; a signal-collecting unit; and pattern recognition software, can also be used as a diagnostic system based on detecting volatile gases given off as metabolites by microorganisms. As an example, these devices are commercially available for the detection of the microorganisms causing bacterial pharyngitis.

Although, as discussed above, there are a number of biosensors on the market today, the following technical obstacles have limited them with respect to providing a quintessential biosensor. These technical obstacles include, but are not limited to: (1) stability of the bio-receptor; (2) assay sensitivity; (3) variation in sensitivity; Specificity of analytic detection; Noise interference; Miniaturization; viable cells count; and Time for assay protocol. In addition to this, the paradigm for threat detection used by many devices does not adequately account for the nature of aerosol generation. Any technique specifically designed for the purpose of aerosol generation will yield a different, usually narrower, particle size spectrum than the "normal" background size spectrum. Therefore, there is a need in the art for a system and method that detects a specific size spectrum and will alert the user to the presence of extraneous, possibly threatening agents.

SUMMARY OF THE INVENTION

The present invention, the Nebulized Airborne Biohazard Stage Alert (NABSA), determines the viability of particles using a fluorometer with a dye specifically created to react fluorescently when bonded with viable particles. The NABSA is a system and method comprised of three stages or modules. A Particle Counting Module, which is a Particle Counting Module, relates to detecting particles sized above one micrometer using an Optical Particle Counter (OPC). Once a Particle Counting Module detects a possible threat it triggers a Fluorescence. Detection Module, which will employ a fluorescence detector to determine the viability of biologic activity in a particular sample. Should the sample be determined to contain biological material, a Fluorescence Detection Module will trigger a Comparison Module to directly measure the threat by comparing it with the most common biowarfare agents (BWA). In addition, the present invention also provides means for outputting this information via at least one of a serial link, visual display, analog output, radio link, or audio output.

The NABSA is unconcerned with reporting the actual size of the particle, and is instead only responsible for signaling when detecting the introduction of a particles within the span of at least 0.5 to 2 micrometers at a higher than average particle number concentration. Once aware of such a potential threat, the NABSA employs a fluorescence detector and a specialized non-fluorescent dye, which when combined with microbes becomes fluorescent, to determine whether the amount of overall biologic activity in a particular sample has increased significantly over previous background samples. If the particles are viable the second stage triggers the third stage that performs the determination of the identity of common biowarfare agents (BWA), both toxins and pathogens.

The system and method of the present invention leads to improved bio-detection for a lower cost per square area and provides a higher degree of confidence of threat detection. In particular, using all three stages of the present invention in succession will implement a method for BWA bio-detection that uses the sizes and amount of the particles. In contrast to other background art methods which directly measure the masses of the particles to determine the threat, the system and method of the present invention will give an orthogonal measure aimed at delineating the carriers and not the specific agents. Therefore, the present invention provides a more dependable method of evaluating the threats and empowers administrators with the ability to take action more quickly and effectively.

One embodiment of the present invention is a system or apparatus configured to detect and assess threats due to nebulized biological threats, comprising: a Particle Counting Module configured to detect particles at least one micrometer in diameter; a Fluorescence Detection Module configured to determine whether the particles are biological substance; and a Comparison Module configured to identify whether the biological substance is a bio-warfare agent by comparing with commonly known bio-warfare agents.

In addition, preferably the particles are sized by a Particle Counting Module using an optical particle counter. Further, preferably, the optical particle counter further comprises: a light source that provides a uniform light beam; a focusing lens to focus the light source onto the beam stop; a flow tube for the particles to flow through; a beam stop to capture the light not scattered by the particles; and a photo detector to detect light scatter beyond the beam stop. Moreover, preferably a communication subsystem will be at least one of wired or wireless.

Preferably, the photo detector reports whether a particle of a target range is detected by the amplifier board. Preferably, the amplifier board amplifies and filters the signal and the control board receives the signal from the amplifier board. In addition, preferably the control board will reinitialize the amplifier board either upon startup of the system, or upon randomized time periods and the control board will send the signal on to the communication board either at either low, medium, or high send rates. Further, preferably the control board will keep count of particles within the target range detected and determine when the count goes beyond a safe threshold.

Preferably, a Fluorescence Detection Module will implement a fluorescence detector and a collection substrate will determine whether the amount of overall biologic activity in a particular sample has increased significantly over previous background samples. Moreover, preferably, upon determination that a threat is detected, a Comparison Module compares the detected substance with the most common bio-warfare agents, comprising at least toxins and microbial pathogens.

Another embodiment of the present invention is a method for bio-detection comprising: waiting for a broadcast signal; receiving a broadcast signal and storing and re-broadcasting previous results of the OPC to other NABSA systems; determining whether a broadcast signal is received from other NABSA systems; determining the signal type results detected by each NABSA system in a network; sampling and reading all the signal type results from the NABSA systems to the data monitor; evaluating the sampling results in the data monitor by comparing to predetermined warning thresholds; and determining whether the sampling rate should be decreased or increased.

In addition, the method of the present invention, preferably comprises waiting for a signal from a Particle Counting Module indicating that a potential threat is detected; adding a non-fluorescent dye to the samples; illuminating the samples by a UV light source to examine for fluorescence; detecting fluorescence with a fluorometer; drawing an air sample for testing; employing a speciation method, such as Polymerase Chain Reaction; and comparing the result to the common biological warfare agents.

In yet another embodiment of the present invention, threat events shall comprise a "high threat alert" when all modules signal an occurrence simultaneously; a "moderate threat potential" when the first two modules together signal an event or if the third module alone signals an event; and a "threat threshold occurrence" if either one of the first two modules singly signals an event.

While the NABSA system is most effective when implemented with three stages, a Particle Counting Module could operate with a Fluorescence Detection Module alone, could operate with a Comparison Module alone, or any of the stages could operate individually. However, when operating with only one or two of the three stages, there is a higher probability of a false positive that could lead to unnecessary and potentially costly panic or a false negative which could lead to the more significant cost of lives which could otherwise be saved.

BRIEF DESCRIPTION OF THE DRAWINGS

The invention can be described in greater detail with the aid of the following drawings.

FIG. 2. is an exemplary data flow diagram presenting how the signal moves through the communications subsystem.

DETAILED DESCRIPTION OF THE PREFERRED EMBODIMENT

Figure 1:
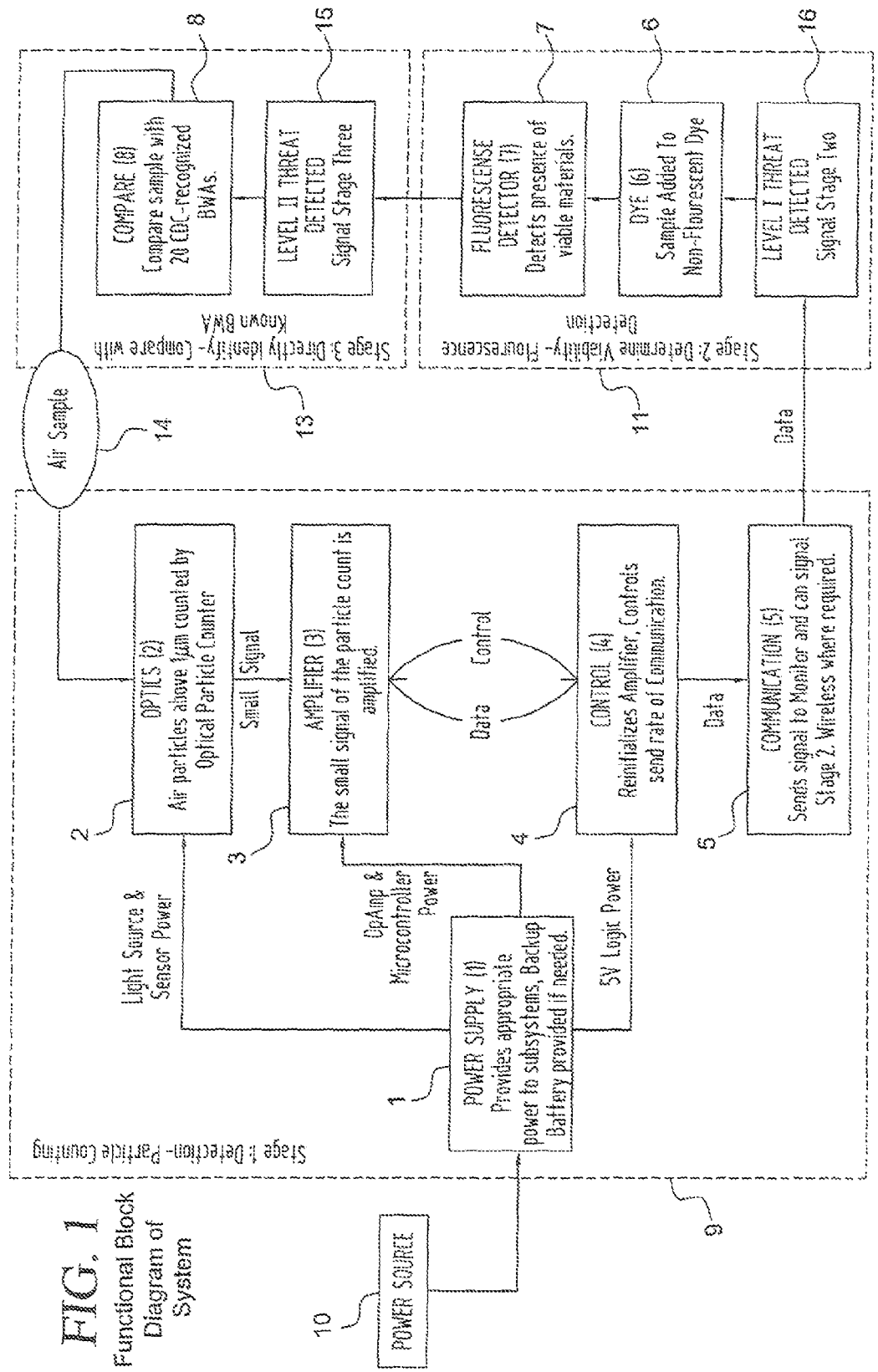
FIG. 1. is an exemplary block diagram showing the functional blocks used to implement the apparatus and method of the present invention.

The exemplary system block diagram of FIG. 1 shows the apparatus of the present invention. In particular, FIG. 1 presents the various, stages/modules of the NABSA system and their interactions. In addition, the NABSA system includes the functions of power supply, amplifier, filtering, DC-cancellation, signal processing of a photometer device, and communications.

A Particle Counting Module 9 comprising a light scattering photometer capable of classifying particles above one micrometer in size. This classification is done in real time with constant analysis and storage of the results. A Particle Counting Module is able to determine the introduction of a specific narrow size spectrum aerosol at a higher than average particle number concentration and is widely disseminating to alert to the occurrence of a potential threat.

For a Particle Counting Module 9, the power source 10 is the main line-fed supply (e.g., 120 VAC) used by the OPC. The power supply 1 converts the input voltage into the voltages needed for the optics 2, amplifier 3, control 4 and communications 5 subsystem functions. The NABSA system should only draw upon the elective battery backup source when the main power source is not available. A switching mechanism (not shown) will handle the alternating between the main and battery power sources. The battery backup is only required for the NABSA systems not monitoring planes or vehicles. NABSA systems for these applications will only need to monitor inside the plane or vehicle when the plane or vehicle and may draw from the power supply of the plane of vehicle. NABSA systems running outside or within buildings will run continuously and only need to run on battery backup in the case of a power failure.

The optics 2 is a portion of the particle counter. The optics 2 consists of an energy source, a laser diode, a photo sensor, a beam stop, and a focusing lens. The beam stop blocks all light that is not scattered by the particles. The lens focuses the light source to the beam stop. Should a particle above a micrometer disrupt the beam, the scattered light will miss the beam stop and be sensed by the photo sensor. The photo sensor is for example, but not limited to, a photo transistor or a photo diode.

The amplifier 3 receives the signal from the photo sensor of the optics 2 subsystem. The amplifier 3 may comprise, but is not limited to, four amplifying stages and six filtering stages. The filtering takes place between each amplification stage. The first and last amplification stages have gains set by fixed resistors; the two middle stages are programmable gain amplifiers set by a microcontroller unit (MCU).

The control board 4 handles the re-initialization of the amplifier 3 and the input values. Re-initialization occurs during power up and some implementations will have the capability to re-initialize on command. For the NABSA system to be installed outdoors or inside buildings, the control board 4 will also be responsible for determining the send rate, which will increase or decrease at preset thresholds of the particle counts. NABSA systems installed inside of vehicles and planes have wired communication, and may not require different send rates.

Should a potential threat be detected, a Fluorescence Detection Module 11 will determine whether the amount of overall biologic activity in a particular sample has increased significantly over previous background samples. A fluorescence detector and DNA-based technology could quickly detect suspicious levels of bacteria, bacterial spores and many viruses. The sample, which can be drawn in series with a Particle Counting Module 9, will be exposed to a dye that is actively or passively internalized by the cells and has fluorescence properties that are measurably altered when bound to target components of viable substances. If the particles fluoresce, they can be classified as living organisms, a characteristic of biological agents.

A Fluorescence Detection Module 11 comprising a collection substrate and a fluorometer which is used to detect the fluorescence of the sample when exposed to the dye, and compare this sample with a control non-viable substance. The second stage is less widely disseminated in order to detect all threats, but is still particular enough to still rule out most hoaxes. This stage can then be used to trigger a Comparison Module 13 to attempt to compare the sample with known BWAs.

In a Comparison Module 13, the sampled air particles, which are drawn in parallel with Stages One and Two in such that the particles have not already been exposed to the fluorescent dye, are compared to the most commonly known bio-warfare agents, such as, but not limited to toxins and microbial pathogens. Once the BWA has been determined, appropriate counteractive measures can be put into action.

The technology used for a Comparison Module 13 provides an additional improvement over background art techniques for bio-detection. A Comparison Module 13, in association with the other two modules, provides a method for evaluating the threat matrix comprising the steps of: determining a significant increase in the overall particle concentration and a spike in a particular range of particle size within a short time span; determining the presence of increased biologic activity in the collected material during the same short time span; and recognizing certain known biological weapons agents in the air streams.

The NABSA system and method of the present invention could also be used at outdoor functions with the addition of a wireless communication system and a battery backup. The NABSA system and method of the present invention would be line-fed by widely available standard power sources (e.g., 120 VAC) and include a battery backup required to maintain power in case of possible power failures. The NABSA could wirelessly communicate with a central data monitor, allowing a broad outdoor or indoor area to be monitored. By installing the detectors of a NABSA system on street corners, constant monitoring of major metropolitan areas could be provided and a swift response with appropriate actions ensured should a bio-hazard attack occur.

FIG. 2 shows an exemplary flow diagram for a method for communication and bio-detection that is used in the present invention. In particular, FIG. 2 shows an example of how the data will flow through the Communications MCU 5 and how the bio-detection analysis proceeds. The Communication MCU 5 of FIG. 1 controls communication to OPC devices in additional NABSA systems and the passes on information provided by previous NABSAs in a network of NABSA systems. In addition, the Communication MCU 5 handles state changes of the OPC device. State changes are further defined in terms of the transmission rates of the NABSA system.

During initialization of communication amongst NABSA systems performing the method for bio-detection of the present invention, the Communication MCU 5 will wait for a broadcast signal, as shown in step 101 of FIG. 2. This broadcast signal will be coming from either any other NABSA system or the data monitor. In step 103 of FIG. 2, the broadcast signal is received by the OPC. At this time, the previous results of the OPC are stored and the results are then rebroadcast to other NABSA systems in step 105. A check is made to determine whether a broadcast signal is received from other NBSA systems in step 107. Next, the signal type detected by each NBSA system in a network of NABSA systems is identified, as shown in step 109 of FIG. 2. This sampling of results occurs until all the results from the NBSA systems are read by the data monitor in step 111. The sampling time is determined in step 113. The sampling time may be implemented as an interrupt function and allows the identification processes to be paused in order for a sensor to perform further classification analysis. Once sampling has occurred, the Communication MCU 5 requests the data from the amplifier in step 115. This data is then transmitted back to the data monitor for evaluation in step 117. After transmission, the count value is compared to the warning thresholds in step 119 to determine whether or not the sampling rate should be decreased, as in step 121, or increased, as in step 123.

Further steps in the method for bio-detection process and classification analysis of the present invention are performed when A Fluorescence Detection Module 11 is installed in-line with a Particle Counting Module 9. A Fluorescence Detection Module 11 will wait for a signal from a Particle Counting Module indicating that a potential threat is detected. Once a Fluorescence Detection Module 11 is signaled, the sample is added to a non-fluorescent dye in the dye subsystem 6, shown in FIG. 1, which when exposed will bind to a cellular component found in all microbes. When the binding occurs, the dye molecules change shape and become fluorescent when the dyed sample is illuminated by a UV light source to examine for fluorescence. The fluorometer 7 shown in FIG. 1 can then be used detect these viable particles.

Further analysis in the method for bio-detection of the present invention occurs when a Comparison Module 13 is triggered by a Fluorescence Detection Module 11 upon the discovery of viable particles in the air sample. A Comparison Module 13 then draws its own air sample to ensure an unaffected sample for testing and employs a speciation method. Speciation methods, include but are not limited to Polymerase Chain Reaction (PCR), and are employed to determine the DNA of the viable particle. This data is compared to the most common BWAs in the Compare subsystem 8 shown in FIG. 1.

A Particle Counting Module 9 is the least expensive stage and when operating singly, will report any occurrence of detected particles above one micrometer within a few seconds. Thus, a Particle Counting Module 9 will signal alerts not only for BWAs released in an aerosol, but also for any detected large particle aerosol release. However, it should be noted that the large particle aerosols are innocuous such as hair spray or cooking oil.

A Fluorescence Detection Module 11, when operating singly, will report the detection of microbial agents. Though a Fluorescence Detection Module 11 is less disseminating than a Particle Counting Module 9, it may also include possible false positives when sensing such non-threatening materials as yeast or sneeze releases. A Fluorescence Detection Module 11 is also typically more expensive to produce than a Particle Counting Module 9 and requires at most 20 minutes to detect a threat. A Fluorescence Detection Module 11 also requires more maintenance.

A Comparison Module 13 is the least disseminating, and will report the definite presence of one of the known BWAs. However, a Comparison Module 13 is limited by its low sensitivity of detection and by its specificity of what it can detect. Thus, is possible for a Comparison Module 13 to be reporting a false negative if it fails to detect a known threat, or if the threat is something currently unknown. Of the three, a Comparison Module 13 is the most expensive to produce and most complex to maintain. In addition it takes a Comparison Module 13 the longest to confirm the introduction of a threat.

By operating a Particle Counting Module 9 and a Fluorescence Detection Module 11 in conjunction, it is possible to determine significant increase in overall viable particle concentration with a spike in the large particle size range of interest within a short span of time. The generation of large viable particles is unusual and likely indicates the presence of a threatening BWA. However, without a Comparison Module 13 there is less assurance that what is being detected is an actual. BWA.

By implementing a Particle Counting Module 9 and a Comparison Module 13 in conjunction, every time a Particle Counting Module 9 detects an aerosol it would signal the Comparison Module 13. Such a system would alert for possible and definite threats. However, with the aforementioned weaknesses of a Comparison Module 13 there would still be less assurance about false negatives. An example of one of these false negatives is when a Particle Counting Module 9 detects a threat missed by a Comparison Module 13 it might not be given the weight needed if it had a Fluorescence Detection Module 11 in support.

By working a Fluorescence Detection Module 11 and a Comparison Module 13 in conjunction, it would be possible to detect BWAs. However, this configuration would not provide the fast response of a Particle Counting Module 9 and would not detect the introduction of a specific narrow sized aerosol. Thus, there is a higher possibility of false negatives that could otherwise be detected.

The NABSA system and method of the present invention could be deployed in ventilation systems of buildings or in the ventilation system of commercial carriers such as, busses, subways and airplane. In the case of a commercial carrier, the introduction of a biological aerosol generator could be accomplished in a pocket-sized, simple and inexpensive form. Such a biological aerosol generator could silently contaminate hundreds of individuals as well as spread further contamination from their clothes and their subsequent infection. This threat could be immediately detected with either the first stage or the first and second stages of the system and method of the present invention. The system and method of the present invention could monitor the re-circulated air within the cabin of the commercial carrier or building; sense a potential threat; and allow the threat to be assessed immediately so the decision makers can conduct the appropriate actions.

The foregoing description illustrates and describes the present invention. Additionally, the disclosure shows and describes only the preferred embodiments of the invention, but as mentioned above, it is to be understood that the invention is capable of use in various other combinations, modifications, and environments and is capable of changes or modifications within the scope of the inventive concept as expressed herein, commensurate with the above teachings and/or skill or knowledge of the relevant art. The embodiments described hereinabove are further intended to explain best modes known of practicing the invention and to enable others skilled in the art to utilize the invention in such or other embodiments and with the various modifications required by the particular applications or uses of the invention. Accordingly, the description is not intended to limit the invention to the form or application disclosed herein. Also, it is intended that the appended claims be construed to include alternative embodiments.

What is claimed is:

1. A method for bio-detection comprising:
    waiting for a broadcast signal;
    receiving a broadcast signal and storing and re-broadcasting previous results of the OPC to other NABSA systems;
    determining whether a broadcast signal is received from other NABSA systems;
    determining the signal type results detected by each NABSA system in a network;
    sampling and reading all the signal type results from the NABSA systems to the data monitor;
    evaluating the sampling results in the data monitor by comparing to predetermined warning thresholds;
    determining whether the sampling rate should be decreased or increased;
    waiting for a signal from a Particle Counting Module indicating that a potential threat is detected;
    adding a non-fluorescent dye to the samples;
    illuminating the samples by a UV light source to examine for fluorescence;
    detecting fluorescence with a fluorometer;
    drawing an air sample for testing;
    employing a speciation method for testing, such as Polymerase Chain Reaction; and
    comparing the result to common biological warfare agents.

* * * * *